United States Patent [19]

Arlt

[11] 4,045,481
[45] Aug. 30, 1977

[54] PROCESS FOR THE PREPARATION OF CHLORINATED ISOCYANIDE DICHLORIDE

[75] Inventor: Dieter Arlt, Cologne-Buchheim, Germany

[73] Assignee: Bayer Aktiengesellschaft, Leverkusen, Germany

[21] Appl. No.: 596,866

[22] Filed: July 17, 1975

Related U.S. Application Data

[63] Continuation of Ser. No. 793,926, Jan. 21, 1969, abandoned.

[30] Foreign Application Priority Data

Feb. 2, 1968 Germany .......................... 1668089

[51] Int. Cl.$^2$ .......................................... C07C 119/00
[52] U.S. Cl. ................................. 260/566 D; 71/121; 424/325

[58] Field of Search .................................. 260/566 D

[56] References Cited

FOREIGN PATENT DOCUMENTS

| 741,794 | 8/1966 | Canada .......................... 260/566 D |
| 952,805 | 3/1964 | United Kingdom ........... 260/566 D |

OTHER PUBLICATIONS

Derwent Belgian Patent Reports No. 41/68 ss5, p. 1, (Nov. 13, 1968).

*Primary Examiner*—Gerald A. Schwartz
*Attorney, Agent, or Firm*—Burgess, Dinklage & Sprung

[57] ABSTRACT

Disclosed is a process for preparing chlorinated isocyanide dichlorides comprising reacting an olefin with at least equimolar quantities of chlorine and cyanogen chloride at a temperature of from −30° C to about 70° C in the presence of a Friedel-Crafts catalyst.

5 Claims, No Drawings

PROCESS FOR THE PREPARATION OF CHLORINATED ISOCYANIDE DICHLORIDE

This is a continuation of application Ser. No. 793,926 filed Jan. 21, 1969, now abandoned.

The preparation of chloroalkylisocyanide dichlorides from chlorine, cyanogen chloride and olefinic compounds has been disclosed in Belgian Patent No. 713,292.

A process for the preparation of chlorinated isocyanide dichloride has now been found wherein an olefin of the general formula

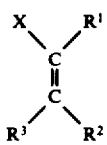

in which

X represents halogen, and the radicals $R^1$, $R^2$ and $R^3$ are equal or different and represent hydrogen, a substituted or unsubstituted alkyl or cycloalkyl radical or a substituted or unsubstituted aromatic radical, or $R^1$ and $R^2$ together are part of a carbocyclic or aromatic ring system, is reacted with at least equimolar quantities of chlorine and cyanogen chloride at a temperature of from −30° C. to about 70° C. in the presence of a Friedel-Crafts catalyst. The reaction may be effective in an inert organic solvent.

If, for example, chlorine is reacted with vinyl chloride in liquid cyanogen chloride at a temperature of about 0° C. in the absence of catalysts, trichloroethane is produced exclusively. In the presence of Friedel-Crafts catalysts, 1,2-dichloroethylisocyanide dichloride is predominantly obtained. It is especially surprising that little or no cyanuric chloride is produced in the process according to the invention since Friedel-Crafts catalysts favour the trimerisation of cyanogen chloride.

Examples of suitable alkyl or cycloalkyl radicals which are optionally substituted are straight-chain or branched alkyl radicals which have 1 - 12, and preferably 1 - 6, carbon atoms. Suitable cycloaliphatic radicals to be mentioned are those which have 5 - 12 and preferably 5- 6 carbon atoms in the ring system. Suitable substituents on the alkyl or cycloalkyl radical are, for example, $NO_2$, halogens (preferably fluorine, chlorine or bromine), $-N=CCl_2$ and alkoxy (preferably 1 - 4 carbon atoms).

The sum of carbon atoms in radicals $R^1$ to $R^3$ is generally not more than 15. The optionally substituted aromatic radicals are advantageously those which have up to 10 carbon atoms in the ring system (phenyl and naphthyl is especially advantageous), generally not more than two of the radicals $R^1$ and $R^3$ representing an aromatic radical. Suitable substituents of the aromatic radical are $NO_2$, halogens (preferably fluorine, chlorine or bromine). $—N=CCl_2$ or alkoxy (preferably 1 - 4 carbon atoms). It is preferred to use olefinic compounds in which X represents fluorine, chlorine or bromine.

Suitable olefinic compounds which have halogen attached to a C-atom of the double bond are, for example, vinyl chloride, vinyl fluoride, vinyl bromide, 1-chloroprene-(1), α-chlorostyrene and 1-chlorocyclohexene-(1).

The process according to the invention is carried out at a temperature of from about −30° C. to 70° C., preferably between about −10° C. and about 30° C. and especially between about −5° C. and about 10° C., if desired in the presence of inert organic solvents such as methylene chloride, chloroform, carbon tetrachloride and chlorobenzene. Chlorine, olefinic compounds and cyanogen chloride are preferably used in about equimolar quantities. However, an excess of these reactants may be used.

Cyanogen chloride in excess is e.g. especially preferred for use as a solvent.

Suitable catalysts are described in Friedel-Crafts and Related Reactions, Volume I, page 201. The following are mentioned as examples:

$AlCl_3$, $AlBr_3$, $BeCl_2$, $CdCl_2$, $ZnCl_2$, $BF_3$, $BCl_3$, $BBr_3$, $GaCl_3$, $GaBr_3$, $TiCl_4$, $TiBr_4$, $ZrCl_4$, $SnCl_4$, $SnBr_4$, $SbCl_5$, $SbCl_3$, $BiCl_3$, $FeCl_3$, $UCl_4$.

It is especially advantageous to use $AlCl_3$, $BF_3$, $FeCl_3$ or $ZnCl_2$. The catalysts are generally used in quantities of from 0.05% to 10% by weight (preferably 0.1 to 0.5% by weight), based on cyanogen chloride.

The reaction mixture obtained by the process according to the invention can be separated by fractional distillation and the desired reaction product can thereby be isolated.

The compounds according to the invention are new and correspond to the general formula:

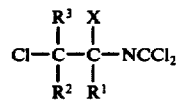

wherein X, $R^1$, $R^2$ and $R^3$ are defined as above.

They are valuable intermediates for the preparation of plastics auxiliary products and may also be used directly as plant protection agents. Plant protecting agents are chemical compounds or preparations which, correctly employed, protect our cultivated plants from sowing to harvest from damages by other organisms (animals and plant parasites). Plant protectives are also herbicides and the agents for influencing the plant growth (Rompp's Chemielexikon, page 4803). Plant protecting agents are, for example, agents having an activity against flies, spiders, mites and fungi (Canadian Pat. No. 741,794).

EXAMPLE 1

360 g. of chlorine (5.2 mol) and 330 g. (5.2 mol) of vinyl chloride are introduced into 300 ml. of cyanogen chloride (= 6 mol) containing 10 g. of aluminium chloride in the course of 4 hours with stirring and cooling. The temperature is maintained at from −5° C. to 5° C. during the reaction. The excess cyanogen chloride is then distilled off at normal pressure. The reaction products are distilled from the reaction vessel in a water-jet vacuum and then fractionated. 540 g (= 55% of the theory) of 1,2-dichloroethyl-isocyanide dichloride of b.p. 71° - 72° C./13 Hg. are obtained.

| Analysis: | $C_3H_3Cl_4N$ (194.89) | | | |
|---|---|---|---|---|
| Calculated: | C 18.5 | H 1.6 | Cl 72.8 | N 7.2 |
| Found: | C 18.7 | H 1.4 | Cl 73.2 | N 7.0 |

EXAMPLE 2

20 g. of anhydrous ferric chloride are dissolved in 500 ml. of cyanogen chloride at −5° C., and 420 g. of chlorine and 450 g. of vinyl chloride are introduced with stirring and cooling to from −5° C. to +0° C. in the course of 5 hours. Excess cyanogen chloride is distilled off at normal pressure and the reaction products are distilled from the reaction vessel at about 15 mm. Hg. 748 g. (= 65% of the theory) of 1,2-dichloroethyl-isocyanide dichloride of boiling point 70° C. to 71° C./13 mm Hg. are obtained from the distilled reaction mixture by fractional vacuum distillation.

EXAMPLE 3

4 g of anhydrous ferric chloride were dissolved in 1.5 l of cyanogen chloride with cooling and stirring. 1000 g of chlorine and 1000 g of vinyl chloride were added within 4 hours. During this time the temperature is kept at 0 to −10° C. By fractional distillation i.v. of the reaction mixture 2200 g of 1,2-dichloro-ethyl-isocyanide dichloride having a boiling point of 65 to 68° C/11 mm Hg. are obtained.

I claim:

1. Process for preparing chlorinated isocyanide dichloride which comprises reacting an olefine selected from the group consisting of vinyl chloride, vinyl fluoride and vinyl bromide, with at least equimolar quantities of chlorine and cyanogen chloride in the presence of a Friedel-Crafts catalyst at a temperature of from about −30° C to about 70° C.

2. Process according to claim 1 wherein said reaction is carried out in an inert organic solvent.

3. A process according to claim 1 wherein excess cyanogen chloride is used as a solvent.

4. Process of claim 1 wherein the olefin is vinyl chloride and the product produced is 1,2-dichloroethyl isocyanide dichloride.

5. Process of claim 1 wherein the olefin is vinyl fluoride and the product produced is 1-chloro-2-fluoroethyl isocyanide dichloride.

* * * * *